United States Patent
Mooney

(10) Patent No.: US 9,415,095 B2
(45) Date of Patent: Aug. 16, 2016

(54) METHOD FOR IMAGE OUTLIER REMOVAL FOR TRANSMISSION ELECTRON MICROSCOPE CAMERAS

(71) Applicant: Paul Mooney, Pleasonton, CA (US)

(72) Inventor: Paul Mooney, Pleasonton, CA (US)

(73) Assignee: Gatan, Inc., Warrendale, PA (US)

( * ) Notice: Subject to any disclaimer, the term of this patent is extended or adjusted under 35 U.S.C. 154(b) by 0 days.

(21) Appl. No.: 14/814,435

(22) Filed: Jul. 30, 2015

(65) Prior Publication Data

US 2015/0332892 A1    Nov. 19, 2015

Related U.S. Application Data

(60) Provisional application No. 62/032,535, filed on Aug. 2, 2014.

(51) Int. Cl.

| A61K 39/00 | (2006.01) |
|---|---|
| H01J 37/26 | (2006.01) |
| A61K 48/00 | (2006.01) |
| C12N 15/09 | (2006.01) |

(52) U.S. Cl.
CPC .............. *A61K 39/00* (2013.01); *A61K 48/00* (2013.01); *H01J 37/263* (2013.01); *C12N 15/09* (2013.01)

(58) Field of Classification Search
USPC ................................................ 250/397, 310
See application file for complete search history.

(56) References Cited

U.S. PATENT DOCUMENTS

| 8,115,824 B2 | 2/2012 | Airey | |
|---|---|---|---|
| 2007/0071171 A1 | 3/2007 | Hayashida et al. | |
| 2007/0085007 A1* | 4/2007 | Araki | H01J 37/265 250/310 |
| 2014/0002662 A1 | 1/2014 | Lewis et al. | |

OTHER PUBLICATIONS

Typke et al, "Stroboscopic image capture: Reducing the dose per frame by a factor of 30 does not prevent beam-induced specimen movement in paraffin", Ultramicroscopy, Elsevier, Amsterdam, NL, vol. 107, No. 2-3, Dec. 22, 2006, pp. 106-115.

Glaeser, R.M. et al, "Images of paraffin monolayer crystals with perfect contrast: Minimization of beam-induced specimen motion", Ultramicroscopy, Elsevier, Amsterdam, NL, vol. 111, No. 2, Jan. 1, 2011, pp. 90-100.

Anonymous: "Single particle analysis—Wikipedia, the free encyclopedia", Jul. 11, 2014, pp. 1-4, https://en.wikipedia.org/w/index.php.

International Search Report for PCT/US2015/043134 mailed Mar. 10, 2016.

\* cited by examiner

*Primary Examiner* — Kiet T Nguyen
(74) *Attorney, Agent, or Firm* — Caesar Rivise, PC

(57) ABSTRACT

Methods are disclosed for removal of outlier pixels from a transmission electron microscopy camera image. One exemplary method includes establishing a desired exposure of n electrons per pixel; exposing the camera to a series of sub-frame exposures to produce a series of sub-frame images; calculating an average image signal of all sub-frame exposures in said series; establishing a threshold selected to achieve a desired number of false positives; evaluating each of said sub-frame exposures for pixels further away from said average than said threshold; and replacing pixels in each of said sub-frame images that exceed said threshold with said average to form corrected sub-frame images.

18 Claims, 6 Drawing Sheets

10

METHOD FOR IMAGE OUTLIER REMOVAL FOR TRANSMISSION ELECTRON MICROSCOPE CAMERAS

CROSS REFERENCE TO RELATED APPLICATION

This utility application claims the benefit under 35 U.S.C. §119(e) of provisional application Ser. No. 62/032,535 filed on Aug. 2, 2014, and entitled "Method for Image outlier Removal for Electron Microscope Cameras." The entire disclosure of the provisional application is incorporated herein by reference.

FIELD OF THE INVENTION

The invention relates generally to the field of electron microscopy image processing.

BACKGROUND OF THE INVENTION

Until recently cameras for electron microscopes have been manufactured exclusively using an indirect imaging method employing either a scintillator to convert an electron image into a light image, some form of optics to capture the light image and transfer it to a plane offset from the scintillator, and a silicon sensor to capture the light image. The optics have been composed either of a fused fiber optic plate or of a lens. Aside from the primary function of light image transfer, the optics also shield the silicon sensor from direct illumination by the electron beam and from x-rays generated through bremsstrahlung by the beam at the scintillator or higher up in the electron microscope column. This secondary function serves to protect the sensor from damage and to prevent image degradation caused by x-rays hitting the sensor. The optic is only partially effective at performing this latter function.

A small fraction of x-rays generated at the scintillator and higher up in the microscope column make it through the optic and a fraction of those are detected directly in the epitaxial layer of the silicon sensor, creating small bright spots at their point of entry which overlay the image formed by the electron beam.

These spots do not contribute to the quality of the image but, rather, detract from it because 1) the random emission angle at the scintillator and subsequent scattering destroy any spatial correlation of the x-rays with the image-signal-bearing electrons which created them at the scintillator and 2) because the directly detected x-ray adds significantly more signal to the image detected at the silicon sensor than the net signal conferred by the incoming electron after scintillation and image transfer by the optic. Thus it is desirable to minimize the number of these x-ray-generated spots.

The primary method for reducing spots has been to increase the mass lying between scintillator and sensor. This method is not fully effective if either the energy of the electron beam is too high or if there is not sufficient room to place enough material between scintillator and sensor. Furthermore, in the case of lens optics, the optical design will dictate the amount of material which might not be sufficient to provide adequate shielding of x-rays.

In addition, aside from scintillator bremsstrahlung x-rays there are other sources of radiation. They include cosmic rays and decay of radioactive elements in the local environment, which also create bright spots in the image. Shielding by the camera housing and by the optics serves to reduce these forms of radiation as well but, as in the case of bremsstrahlung, this is not 100% effective. In addition, direct detection sensors without a scintillator and transfer optics will have issues with detection of stray scatter and other radiation sources which are not described by the statistics of the specimen image and which are disturbing to the image quality.

Thus there is a need for a technique to completely eliminate the spots created in the sensor by x-rays created in the sensor by the incoming electron beam and by other radiation sources. Spots from various sources which do not conform to the statistical characteristics of the intended image are called outliers. An image processing technique for eliminating outliers would address all of the above various sources of radiation-induced spots without regard to origin.

Image processing techniques based on removal of outliers from an integrated exposure are known. In these techniques, local image statistics are evaluated to establish a local expected range of non-outlier values and outliers are identified as those pixels which do not fall in that local expected range. The range is normally established using a multiple of standard deviations which is chosen to minimize false identification of outliers from pixels which do not suffer from a direct radiation detection event. Since in general, the standard deviation or other measure of statistical deviation varies depending on the local illumination strength (which will be referred to here as electron dose per pixel or electron dose for short) and hence also the local specimen image brightness, and since the specimen can change from one image to the next and from one region to the next within one image, the threshold itself has typically been evaluated separately for each image which is to be processed.

There are a number of problems with this approach. First, it relies on the assumption of ergodicity, i.e. that the statistics of a local group of pixels match the statistics of one of those pixels over a series of acquisitions. This assumption breaks down for high-contrast or rapidly varying specimen images. The effect of specimen contrast can be minimized by evaluating statistics of only a small local region around the pixel being tested but this requirement reduces the number of pixels which are used to calculate the average signal level and of the standard deviation used to generate the outlier threshold criterion. This forces a compromise which works well for low-contrast specimens but still breaks down for more difficult image content such as diffraction patterns or images containing sharp edges, allowing high-contrast features in an image (such as diffraction pattern spots) to be falsely identified as radiation event outliers.

A second problem is that as dose level increases, the histogram of ordinary Gaussian noise in the indirect image (the intended, "good" image from scintillator light generation, optical transfer and sensor detection) grows to obscure more and more of the histogram of the directly detected radiation events. In the case of scintillator bremsstrahlung, which is the most important source of outliers in transmission electron microscope imaging, especially at accelerating voltages above 200 kV, the x-ray outlier count rate is proportional to the beam intensity. This effect is illustrated by FIG. 1, which depicts the result of exposing an indirectly coupled transmission electron microscope camera to a 400 kV uniform beam at two different dose levels of approximately 100 and 7000 beam electrons per detector pixel. At each dose, a pair of identical exposures was taken and differenced to remove fixed pattern gain variations from the histogram. To generate the curves in FIG. 1, the histogram of the absolute value of the difference image was divided by the total average dose in the exposure pair to form a normalized histogram with units: pixels per incoming beam electron at a given count rate. The x-axis of the graph represents the absolute magnitude in counts of a pixel's deviation from the image mean whether high or low. Both the low (100 electron per pixel) dose 1 and the high (7000 electrons per pixel) dose 2 histograms can be seen to consist of two components each: a Gaussian-shaped 3 (inverse parabola in the log display) indirect image noise distribution and a decaying exponential 4 (downward sloping approximately line-shaped in the log display) distribution of x-ray-generated outliers. The normalized noise distribution gets wider and lower as beam intensity goes higher while the normalized distribution of counts at a given pixel per incoming beam electron is constant as predicted for beam-generated bremsstrahlung x-rays in the region of the histogram above the Gaussian distribution. For low dose (100 electrons per pixel) this starts at about 150 counts 5 while for high dose (7000 electrons per pixel) this starts at about 700 counts 6. Thus, at higher doses, a significant portion of the outlier distribution is covered by the Gaussian distribution and can therefore not be discriminated based on an outlier threshold approach. While the argument can be made that if it can't be discriminated it is also not visible and therefore not a problem, outliers near the envelope of the normal distribution can still contribute appreciably to the total noise. In this example, it can be shown that the outliers left in the 7000 electron per pixel image by thresholding at 700 counts instead of 150 counts account for about 5% of the variance in the 7000 electron per pixel power spectrum.

After detection, the simplest method for correction of outliers is to return them to the local mean. An alternative is to set the outlier pixel to a value interpolated from nearest neighbors. For high-contrast images with significant spatial variation, errors can be introduced here as well, in that average-setting and interpolation will both be inaccurate if the image is too rapidly varying as a function of position.

Therefore there is a need for an improved method for providing image outlier detection and correction.

DESCRIPTION OF THE PREFERRED EMBODIMENT OF THE INVENTION

Figure 1:
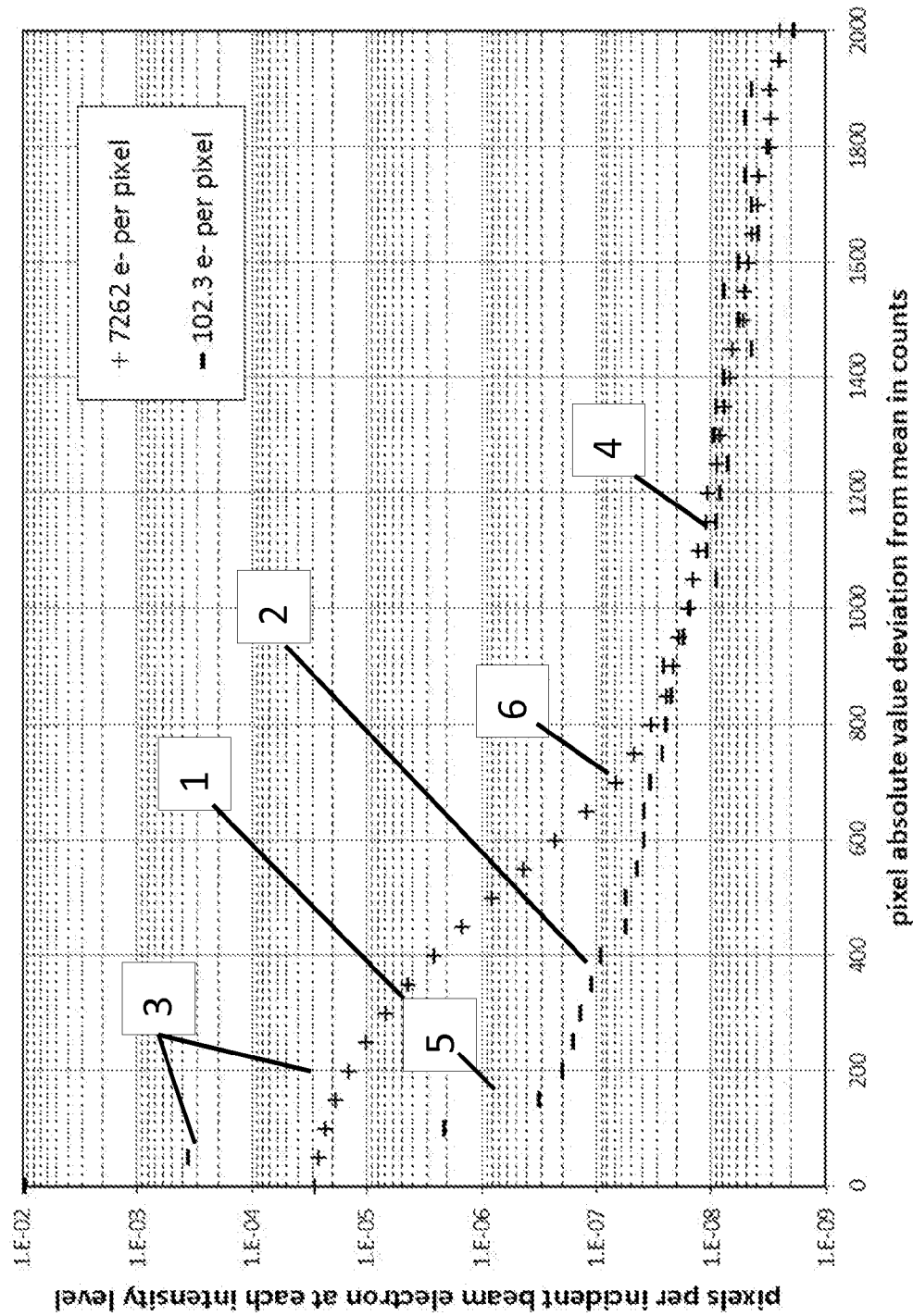
FIG. 1 is a graph of typical pixels per incident beam electron at different intensity levels.
Figure 2:
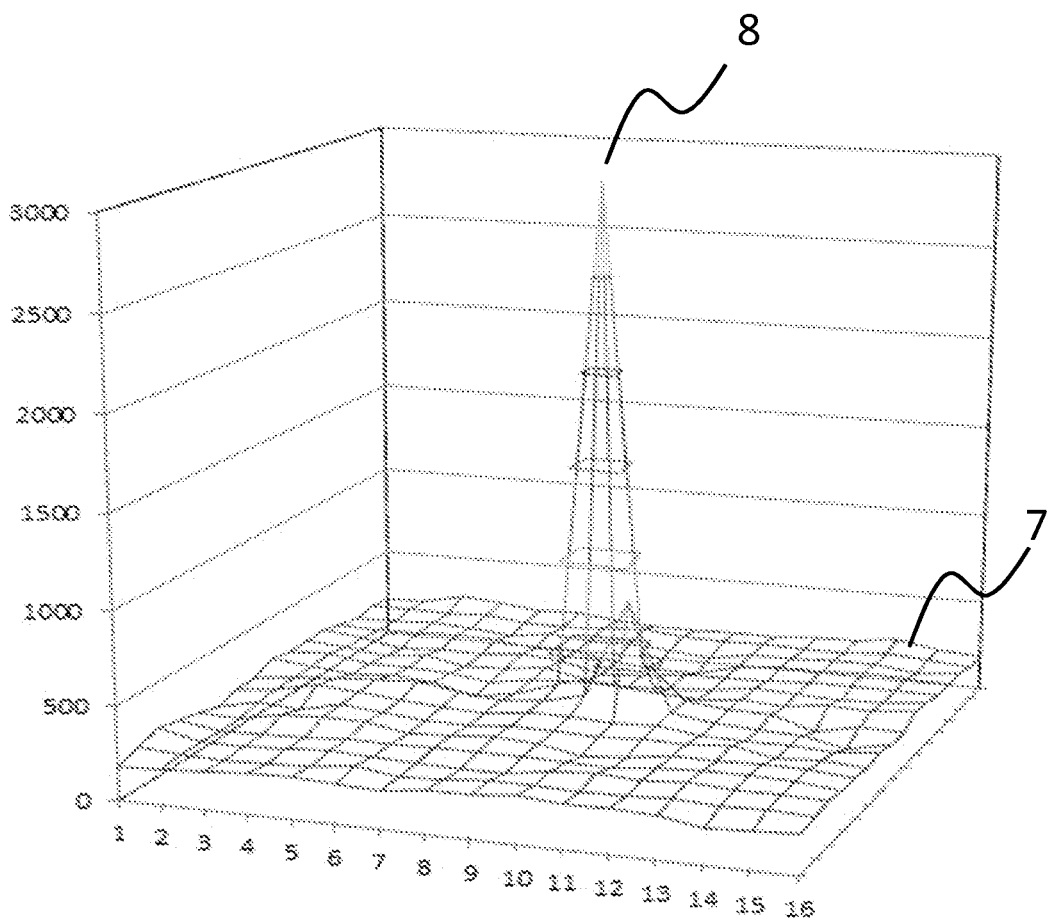
FIG. 2 is a three dimensional graph of an image with pixel intensity displayed in the vertical axis.
Figure 3:
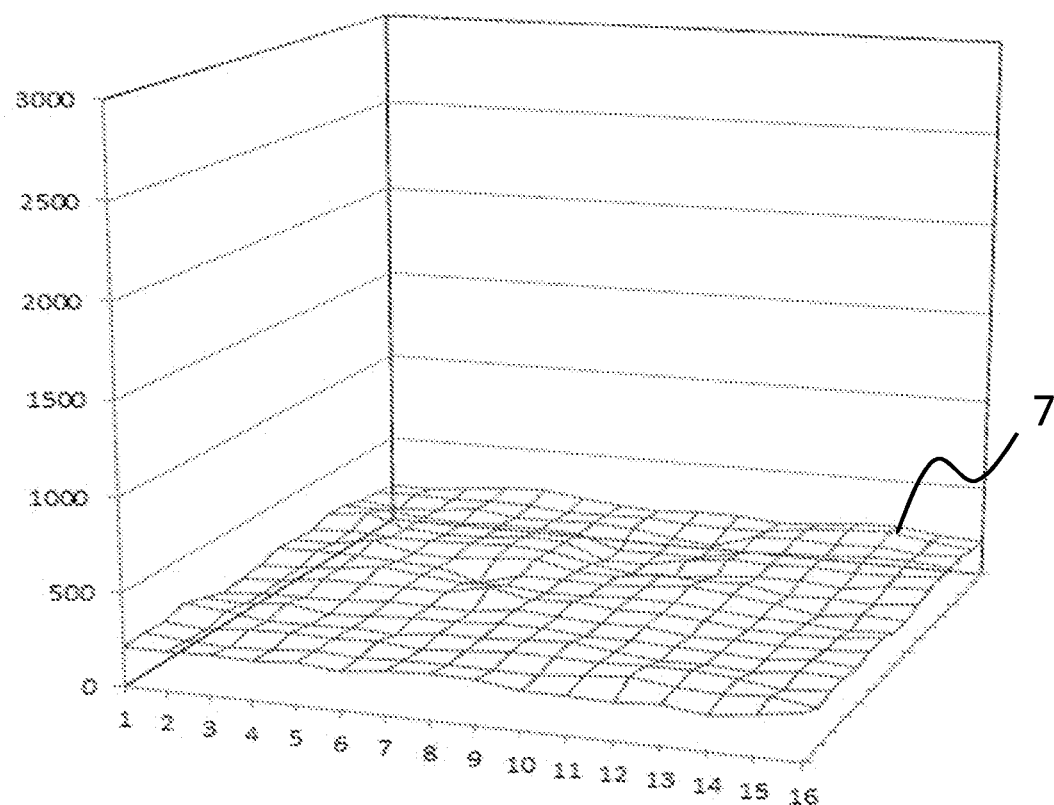
FIG. 3 is a three dimensional graph of an image, with pixel intensity displayed in the vertical axis.
Figure 5:
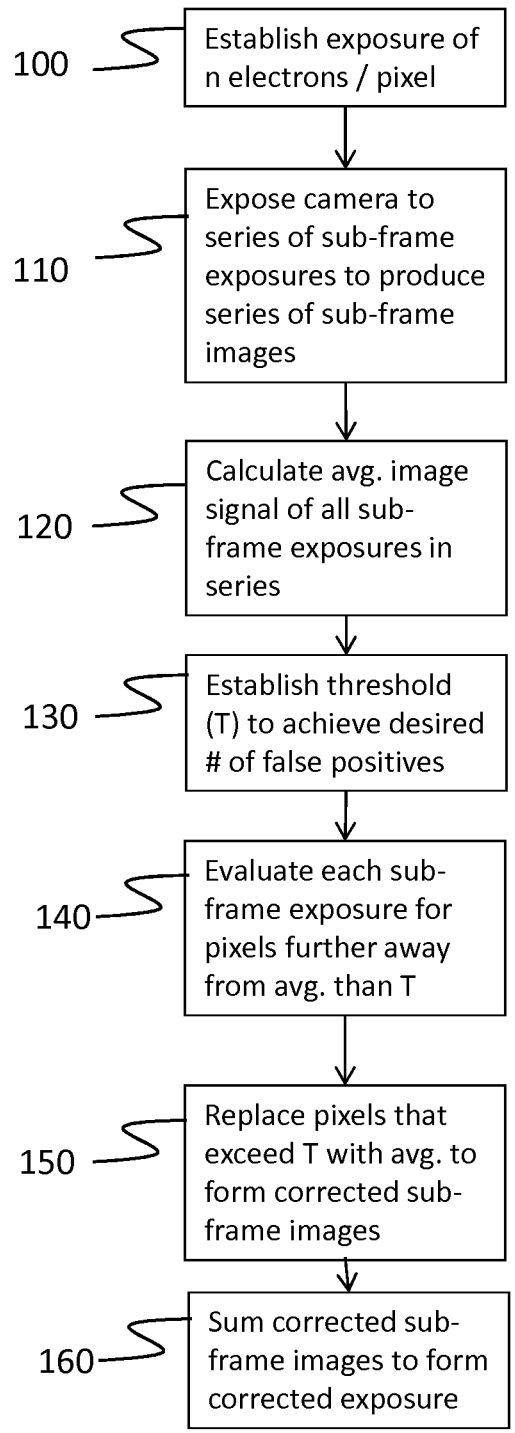
FIG. 5 is an exemplary method of correcting for outlying pixels.

Fractionating the dose of an exposure, i.e. dividing it into a series of sub-exposures which still add up to the same total dose, creates a number of opportunities to improve outlier removal. First, it allows the evaluation of mean and standard deviation for the determination of an outlier threshold on a pixel-by-pixel basis by providing an exposure series for each pixel and thereby avoids reliance of the method on the assumption of ergodicity. In turn, by virtue of making the statistical evaluation pixel-wise, it largely removes the sensitivity to specimen image characteristics. Second, by reducing the dose at which thresholding is done, less of the direct radiation detection histogram is subsumed into the indirect image signal allowing choice of a lower threshold and a more complete removal of unintended radiation signal. Third, since each sub-exposure can be corrected individually, each pixel of the final summed image will have reduced artifacts from replacement of outliers by either average or interpolated values, since typically only a maximum of one of a series of sub-exposures will have been corrected at any given pixel. Even for long ten- or several-hundred sub-exposure sums double (or higher) hits in a given pixel are very rare due to the very low event rate (on the order of $10^{-7}$ to $10^{-6}$ per incoming microscope electron). FIGS. 2 and 3 shows the same detector area in two successive 50 electron uniform illumination exposures at 400 kV displayed as 3-dimensional graphs, with pixel intensity displayed in the third dimension. The low-lying part of the graph in both figures is the uniform illumination pixel intensity 7 and the sharp peak 8 in FIG. 2 the lone outlier. The second exposure, shown in FIG. 3 selected from the next frame at the same location and has no outliers. At this dose (50 electrons per pixel per second) at 400 kV, approximately one event is expected for every 20,000 pixels, or one for every 140×140 pixel area. In the detector area of FIGS. 2 and 3, only one of every 80 frames is expected to have an outlier and the likelihood that two outliers will be on the same pixel in any one frame is one in 400,000,000 ($20,000^2$). It is therefore possible to accumulate excellent statistics on the mean value of each pixel and on the noise level in that pixel over the image series. The following is a description of steps of an exemplary method for producing images and removing outlier pixels. A flow chart for this method is shown in FIG. 5.

Step 1: For a given desired exposure with dose n electrons per pixel 100, split the exposure into s equal sub-exposures 110.

Step 2: Calculate the average image signal of all sub-exposures, $A_{i,j}^0 = \Sigma_k S_{i,j,k}^0 / k$ where the "zero" superscripts mean that this is an initial average based on raw, un-thresholded data. Subscripts i and j are indices over the pixels of each sub-frame in the series of dose-fractionated sub-exposures and k is an index over the series of fractional sub-frames. $A_{i,j}^0$, the average of all images in the dose-fractionated image series, is itself an image 120.

Step 3: Using that average, calculate the standard deviation of the time series of intensities formed at each pixel in the image series, $D_{i,j}^0 = \mathrm{sqrt}(\Sigma_k (S_{i,j,k}^0 - A_{i,j}^0)^2 / (k-1))$. $D_{i,j}^0$, the standard deviation of the image series, like $A_{i,j}^0$, is also an image.

Figure 4:
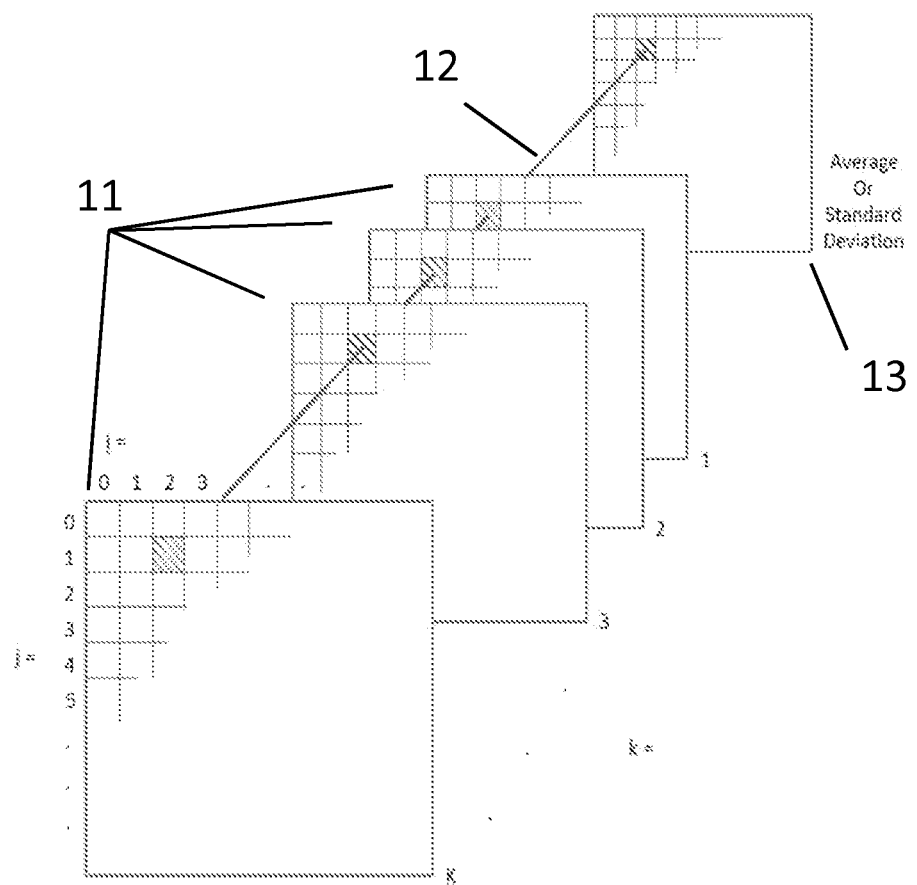
FIG. 4 is a graphical representation of creation of a standard deviation image.

By the same convention as for $A_{i,j}^0$, the superscript "0" means that this is an initial standard deviation calculated from the raw data. Subscripts i and j are indices over the pixels of the standard deviation image. The average of square deviations is formed by dividing by k−1 instead of by k as for the average in order to compensate for the reduction of variation caused by the average $A_{i,j}^0$ following the data for the particular k frames as per standard practice in statistics. The series of sub-exposures and the calculated average image or standard deviation image are shown with their indices in FIG. 4. The image series 11 is a three-dimensional data set. The act of summation, shown acting on pixel (i,j)=(2,1), 12 used in the forming of the average and standard deviation reduces the dimensionality so that the average and the standard deviation are 2-dimensional images.

Step 4: Select a threshold 130 factor x times the calculated standard deviation to achieve the desired number of false positives. As an example, x=3 yields a false positive rate of 1 false outliers for every 730 pixels assuming a perfect Gaussian distribution and a perfect measurement of mean and standard deviation when only positive outliers are discriminated.

Step 5: Evaluate 140 every sub-frame for pixels further away from the average than the threshold $x \times D_{i,j}^0$ pixels. Stated mathematically, the outlier discrimination criterion for a pixel (i,j) in sub-frame k is abs($S_{i,j,k}^0 - A_{i,j}^0$)>x×$D_{i,j}^0$, where "abs" means the function "absolute value." When only positive outliers are to be considered, the absolute value can be omitted. When this criterion is met, the outlier will be removed as in the next step.

Step 6: Replace 150 pixels exceeding the threshold with the pixel time series average $A_{i,j}^0$. Call the series of corrected sub-exposures $S_{i,j,k}^1$.

Step 7: Form the sum $\Sigma_k S_{i,j,k}^1$ to yield the basic time-series outlier-corrected exposure 160.

Multiple Iteration

In a further embodiment, multiple passes are made as follows: Steps 2-6 are repeated using the corrected pixels values to calculate refined average and standard deviation images, $A_{i,j}^p$ and $D_{i,j}^p$, where p is the number of the iteration. The threshold factor x is generalized to a series of valises $x_p$ to allow tightening of the threshold as average and standard deviation calculations become more accurate as outliers are removed on successive iterations. The repeated iterations are terminated either at a predetermined number of iterations (for instance 2) or by a convergence criterion such as abs($A_{i,j}^p - A_{i,j}^{p-1}$)/$A_{i,j}^{p-1}$<ϵ. Where i and j are the indices of the pixel, p is the number of iteration passes and c is the fraction of change allowed at the last iteration.

Running Average

In a further embodiment, a running average is formed. Both the basic technique, described above, and the multi-pass have the issue that no output can appear until the entire data set has been acquired and processed through at least two passes. This is because the calculation of standard deviation cannot start until the average has been calculated and that cannot be done until all the images of the series have been acquired. An alternative approach, appropriate to live view (video) mode, is to use a running average of the last K frames to calculate the pixel-by-pixel average and standard deviation for thresholding the outliers. A running average is most commonly defined by the formula:

$$A_{i,j,this} = 1/R \times (S_{i,j,this}) + (R-1)/R \times (A_{i,j,previous}),$$

where the index k of the previous discussions has been replaced by the words "this" and "previous" to indicate the current acquisition and running average update and the previous running average, respectively, and where R is the effective number of frames averaged by this iterative technique. Since the standard deviation is the square root of the average of squared deviations from the average, i.e. the variance, the running average updating technique is applied to the variance as follows:

$$V_{i,j,this} = \frac{1}{R-1} \times (S_{i,j,this} - A_{i,j,this})^2 + \frac{R-2}{R-1} \times (V_{i,j,previous}),$$

where the number of frames in the denominator has been reduce by one to provide the same compensation for tracking of the finite sample by the average used in the above non-running method. Standard deviation and then threshold would then be calculated from this running average and variance. Both running average and running variance would continue across boundaries between summed exposures on the assumption of modest specimen motion in live view (video) mode. This technique would be most useful and applicable to live view since in that case there is both a need for more rapid determination of average and standard deviation and no problem created by the possibility that the image content might change significantly at the boundary between summed exposures as would usually be the case for still-frame acquisition. It could be used in still frame acquire mode if averaging were started a specified number of frames prior to the start of frame summing, that number determined by a given constant times the effective frames number R.

Non-Destructive Read (NDR)

In a further embodiment, the method is adapted to non-destructive read situations, where the reading of a series of frames on a CMOS active pixel sensor is performed after a single reset of all pixels at the beginning of the series. This method has a number of benefits including noise reduction but creates the need for a different approach when performing outlier removal. With non-destructive read, direct radiation events detected by the device at frame k of an NDR series will remain for all successive frames in that series since no reset will occur after the initial reset. It is therefore necessary, in order to perform outlier discrimination to form a difference between successive frames. Positive outliers found in the difference of frames, $S_{i,j,k} - S_{i,j,k-1}$ must be subtracted from frame k and all successive frames prior to further processing of the non-destructive read image series. Due to the extremely low incidence of radiation event coincidence, it is not necessary to remove events from frame k−1 prior to thresholding of frame k. The preferred implementation of this method is to create K difference images from the K+1 frames of a non-destructive read sequence as follows: for NDR image sequence $S_{i,j,k}$, for k=0, 1, 2, . . . K, form the difference sequence $\Delta_{i,j,k} = S_{i,j,k} - S_{i,j,k-1}$, for k=1,2,3, . . . K. Then perform outlier removal as described in the sections above on those K frames as described in the section on basic outlier removal, above, in sequence steps 2-6. Perform multi-pass refinement if desired and/or one of the other refinements to the basic method. Finally, sum the difference images to reconstitute the NDR sequence but now with outliers removed. This summation operation is defined as follows:

$$C_{i,j,k} = (\Sigma_{\kappa=1}^k \Delta_{i,j,\kappa}) + S_{i,j,0},$$

where κ is a summation index which runs up to the index k of the corrected frame $C_{i,j,k}$. The accuracy of the integral relies on the assumption that the first frame $S_{i,j,0}$ has no outliers by virtue of having been reset immediately prior to read.

Figure 6:
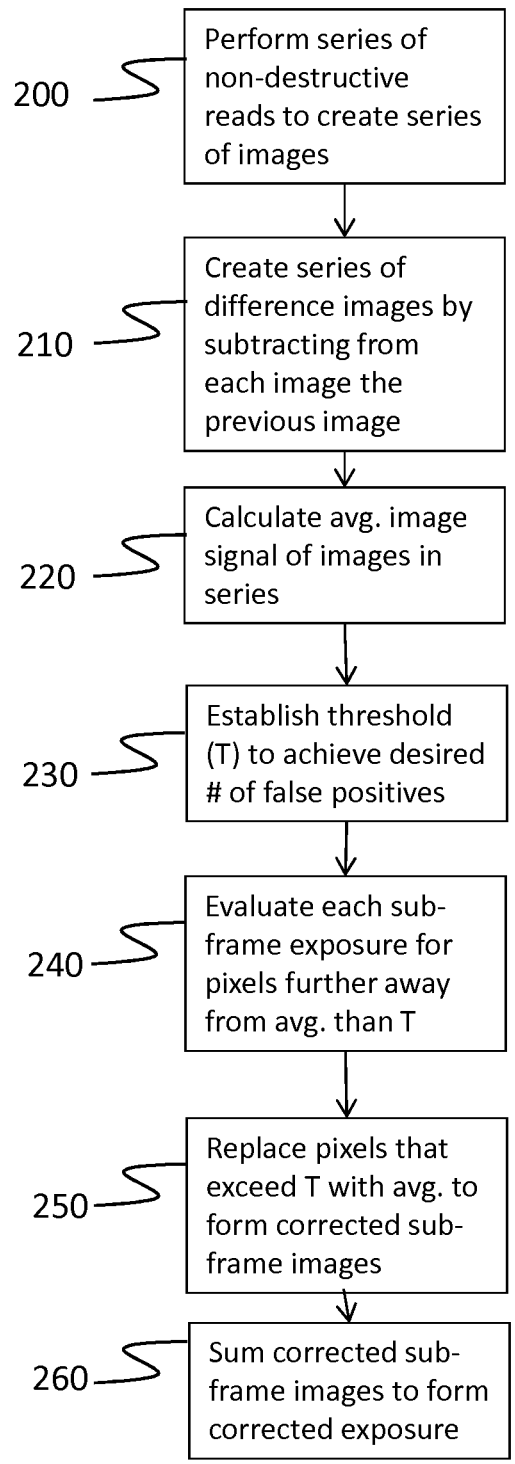
FIG. 6 is an exemplary method of correcting for outlying pixels.

FIG. 6 is a flow chart of an exemplary method of outlier removal for a non-destructive read operation as described above. At step 200, a series of non-destructive reads is performed to create a series of images. At step 210, a series of difference images is created by subtracting from each image (except the first in the series) the previous image. At step 220, an average image signal intensity is calculated across the series of images. At step 230 a threshold is selected to achieve a desired number of false positives. At step 240 each of the sub-frame exposures is evaluated for pixels further away from said average than said threshold. At step 250 pixels in each of the series of images formed subsequent to any of said difference images containing pixels further away from said average than said threshold are replaced to form a corrected series of images. At step 260 corrected sub-frame images are summed to form a corrected exposure.

Two Dimensional Removal

In a further embodiment, the two-dimensional shape characteristics of outlier clusters is used to improve discrimination statistics. In some cases, a radiation detection event affects more than one pixel, depositing charge in a cluster of neighboring pixels with only one or a few pixels having a large signal easily identified as an outlier. The pixels in the radiation detection event pixel cluster with signal lower than the standard outlier threshold may however still have enough signal to reduce the quality of the image signal at those pixels. Thus it can be beneficial to correct these neighboring event pixels even though they aren't discriminated as outliers. One possible way to do this is to establish a lower threshold for neighbors of pixels which are outliers of the main threshold. Those pixels would then be set to the average of that pixel's image series average, not the average of the large outlier neighbor.

Predictive Standard Deviation

Standard deviation of electron signal in a transmission electron microscope can be accurately estimated from average dose level with the equation $D_{i,j} = \sqrt{F_{i,j}^{ref} + v^{ref} \times A_{i,j}^{previousr}}$, where the proportionality constant $v^{ref}$ and the "fog" level $F_{i,j}^{ref}$ are determined beforehand and are stored as references. This estimate can be more accurate than a direct measurement because it follows the statistics of sampled mean $\propto \sigma^2/k$ rather than the statistics of sampled variance $\propto \sigma^4/(k-1)$, where k is the number of samples in the time series and a is the true variance that is to be measured or estimated. This equation allows the pixel-by-pixel standard deviation calculation from the image series to be eliminated, thereby reducing the basic method to a single pass and more than halving the processing time of the multi-pass and running average methods. The technique for reference generation can be performed offline with arbitrarily large doses and can therefore be estimated with lower noise than live estimates performed on the data itself. This allows more accurate estimates of the standard deviation. This in turn allows outliers to be accurately thresholded for exposures with smaller numbers of sub-frames or smaller total doses for which the live data standard deviation estimate can be noisier.

I claim:

1. A method for removal of outlier pixels from a transmission electron microscopy camera image comprising:
   a. establishing a desired exposure of n electrons per pixel;
   b. exposing the camera to a series of sub-frame exposures to produce a series of sub-frame images;
   c. calculating an average image signal of all sub-frame exposures in said series;
   d. establishing a threshold selected to achieve a desired number of false positives;
   e. evaluating each of said sub-frame exposures for pixels further away from said average than said threshold; and
   f. replacing pixels in each of said sub-frame images that exceed said threshold with said average to form corrected sub-frame images.

2. The method of claim 1, further comprising:
   g. calculating a standard deviation of series of exposures for each pixel location in said series of exposures;
   and wherein said threshold is related by a threshold factor to said calculated standard deviation.

3. The method of claim 2, wherein said average is a running average.

4. The method of claim 3, further comprising
   g. calculating a running variance from the series of exposures and from said running average and calculating a running average standard deviation of said series of exposures for each pixel location in said series of exposures from said running variance;
   and wherein said threshold is related by a threshold factor to said calculated standard deviation.

5. The method of claim 1, further comprising the step of:
   h. summing said corrected sub-frame images to form a corrected exposure.

6. The method of claim 5, wherein steps c through f are repeated prior to performing step h.

7. The method of claim 1, wherein said sub-frame exposures are of equal intensity.

8. The method of claim 1, further comprising:
   g. calculating a standard deviation of series of exposures for each pixel location in said series of exposures;
   and wherein said threshold is related by a threshold factor to said calculated standard deviation.

9. The method of claim 8, further comprising the step of:
   h. summing said corrected sub-frame images to form a corrected exposure.

10. The method of claim 8 where the standard deviation is calculated from said average image signal through use of a linear relation comprising multiplying said average image signal by a proportionality factor and adding a dark background noise level, where said proportionality factor and dark background level are references generated prior to imaging a sample.

11. The method of claim 10, further comprising the step of:
    h. summing said corrected sub-frame images to form a corrected exposure.

12. The method of claim 1, further comprising establishing a second threshold for evaluating neighboring pixels near said pixels further away from said average than said threshold and replacing said neighboring pixels that are further away from said average than said second threshold.

13. A method for removal of outlier pixels from a transmission electron microscopy camera image formed by a non-destructive read sequence comprising:
    a. performing a series of non-destructive reads to create a series of images beginning with a first image and including at least one subsequent image;
    b. creating a series of difference images by subtracting from each image, except the first image, the previously read image;
    c. calculating an average image signal intensity across said series of images;
    d. establishing a threshold selected to achieve a desired number of false positives;
    e. evaluating each of sub-frame exposures for pixels further away from said average than said threshold; and
    f. replacing pixels in each of said series of images formed subsequent to any of said difference images containing pixels further away from said average than said threshold to form a corrected series of images.

14. The method of claim 13, further comprising the step of:
    g. summing said corrected series of images to form a corrected exposure.

15. The method of claim 14, wherein steps c through f are repeated prior to performing step g.

16. The method of claim 13, further comprising
    g. calculating a standard deviation of said series of images for each pixel location in said series of images;
    and wherein said threshold is related by a threshold factor to said calculated standard deviation.

17. The method of claim 16, further comprising establishing a second threshold for evaluating neighboring pixels near said pixels further away from said average than said threshold and replacing said neighboring pixels that are further away from said average than said second threshold.

18. The method of claim 13, further comprising establishing a second threshold for evaluating neighboring pixels near said pixels further away from said average than said threshold and replacing said neighboring pixels that are further away from said average than said second threshold.

* * * * *